United States Patent [19]

Warriner

[11] Plant 4,139

[45] Nov. 1, 1977

[54] ROSE PLANT

[75] Inventor: William A. Warriner, Tustin, Calif.

[73] Assignee: Jackson & Perkins Co., Medford, Oreg.

[21] Appl. No.: 742,466

[22] Filed: Nov. 17, 1976

[51] Int. Cl.[2] ..... A01H 5/00

[52] U.S. Cl. ..... Plt./28

[58] Field of Search ..... Plt./27-28

*Primary Examiner*—Robert E. Bagwill

*Attorney, Agent, or Firm*—Klarquist, Sparkman, Campbell, Leigh, Hall & Whinston

[57] ABSTRACT

This invention relates to a novel hybrid tea rose plant characterized by its deep red blossom color with imbricated form, borne on vigorous, upright stems.

1 Drawing Figure

1

The present invention relates to a new and distinct cultivar of rose plant of the hybrid tea class which was originated by me by crossing two unnamed, unreleased, red, hybrid tea cultivars which are part of the group of parent cultivars of roses under my control.

The primary objective of this breeding was to produce a new rose cultivar of the hybrid tea class of strong plant habit, dark red blooms and an above normal abundance of blooms. This objective was substantially achieved along with other desirable improvements as evidenced by the following unique combination of characteristics which are outstanding in this new cultivar and which distinguish it from its parents as well as from all other cultivars of which I am aware:

1. An upright very vigorous plant similar in character to the cultivar Mr. Lincoln, U.S. Plant Pat. No. 2,370, but branching more readily, making a more dense plant.
2. Opening bud color of a deep red with darker, near black, shadings; described in detailed description.
3. Full open color slightly lighter with little or no blackish shading.
4. Little or no fragrance.
5. Classic spiral opening form with overlying petals definitely imbricated.
6. Abundant branching providing more than normal flower production on long, strong stems and peduncles.
7. A moderate amount of large prickles, hooked slightly downward.
8. A good degree of mildew resistance, showing only light effects of the disease.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color terminology in accordance with *Munsell Book of Color,* except where ordinary dictionary significance of color is indicated.

Parentage: Seedling.

*Seed parent.*—Unnamed variety.

*Pollen parent.*—Unnamed variety.

Classification:

*Botanical.*—Rosa hybrid.

*Commercial.*—Hybrid tea.

2

FLOWER

Observations made from specimens grown at Irvine, Calif., in September of 1976.

Blooming habit: Continuous.

Bud:

*Size.*—1¼ inches when petals start to unfurl.

*Form.*—Long, pointed ovoid.

*Color.*—When sepals first divide near Red 5.OR 3/8 shaded irregularly with 5.OR 2/2. When half blown; upper side of petals near 5.OR 3/12; Lower side of petals near 5.OR 3/8.

*Sepals.*—Color: Outer surface Green 5.OG 3/4 overlaid heavily with Red 5.OR 2/6; Inner surface, Green-yellow-green 10.0 GY 6/4 with much whitish tomentum. Three appendaged sepals normally appendaged; two unappendaged sepals smooth edge.

*Receptacle.*—Color: Green 5.OG 3/4; Shape: funnel, very small. Size: small; Surface: smooth.

*Peduncle.*—Length: short; surface: numerous stipitate glands; Color: light green, bronzy; Strength: stiff, heavy.

*Opening.*—Slow, spiral.

Bloom:

*Size.*—Large. Average open size 4 inches.

*Borne.*—Singly.

*Stems.*—Long, strong.

*Form.*—High center. Permanence: retains its form to the end; outer petal edges slightly curled.

*Petalage.*—Number of petals under normal conditions is 30–35.

*Color.*—Center of flower: upper side of petals: Red 5.OR 3/12; reverse side of petals: Red 5.OR 3/8; Base of petals lacking pigment in an area approximately ¼ inch in diameter at point of attachment making this area nearly white on upper side. Red color extends to point of attachment on lower side. General tonality from a distance, Red 5.OR 3/12.

*Variegations.*—Shows an occasional greenish white midrib area on one or two outer petals.

*Discoloration.*—Describe general tonality at end of first day: none; Third day: near Red-purple-red 10.0 RP 3/12.

*Fragrance.*—Little to none.

Petals:

*Texture.*—Thick, leathery.

*Shape.*—Round.

*Form.*—Tips slightly recurved.

*Arrangement.*—Imbricated; Petaloids in center:

few.

*Persistence.*—Drop off cleanly.

*Lastingness.*—On the plant: long; As cut flower: long.

Reproductive parts:

*Stamens, Anthers.*—Large, many; Color: yellow; Arrangement: regular around styles.

*Filaments.*—Color: Pink except white near end adjacent to anthers, yellow basal one-third.

*Pollen.*—Gold yellow.

*Styles.*—Color: pink.

*Stigmas.*—Color: white.

PLANT

Form: Bush.

Growth: Very vigorous, upright, branching.

Foliage: Number of leaflets on normal mid-stem leaves 5, sometimes 7.

*Size.*—Large.

*Quantity.*—Normal.

*Color.*—New foliage: near Red 5.OR 2/2; Old foliage: Green 5.OG 3/4.

*Shape.*—Oval pointed.

*Texture.*—Leathery.

*Edge.*—Serrated.

*Serration.*—Single, small.

*Petiole.*—Rachis: Color: Reddish; Underside: Prickles.

*Stipules.*—Long, smooth.

*Disease resistance.*—Normally resistant to mildew under normal growing conditions at Irvine, Calif.

Wood:

*New wood.*—Color: light green; Bark: Smooth.

*Old wood.*—Color: green; Bark: smooth.

Prickles:

*Quantity.*—On main stalks from base, ordinary; On laterals from stalk, ordinary.

*Form.*—Long and narrow base; long hooked downward.

*Color when young.*—Brown.

*Position.*—Irregular.

Small prickles: None.

I claim:

1. A new and distinct cultivar of rose plant of the hybrid tea class, substantially as herein shown and described, characterized particularly as to novelty by the unique combination of its very vigorous, heavily branched, upright plant; bud and flower color of dark red; little or no fragrance; average number of downward hooked prickles; and a goodly degree of mildew resistance.

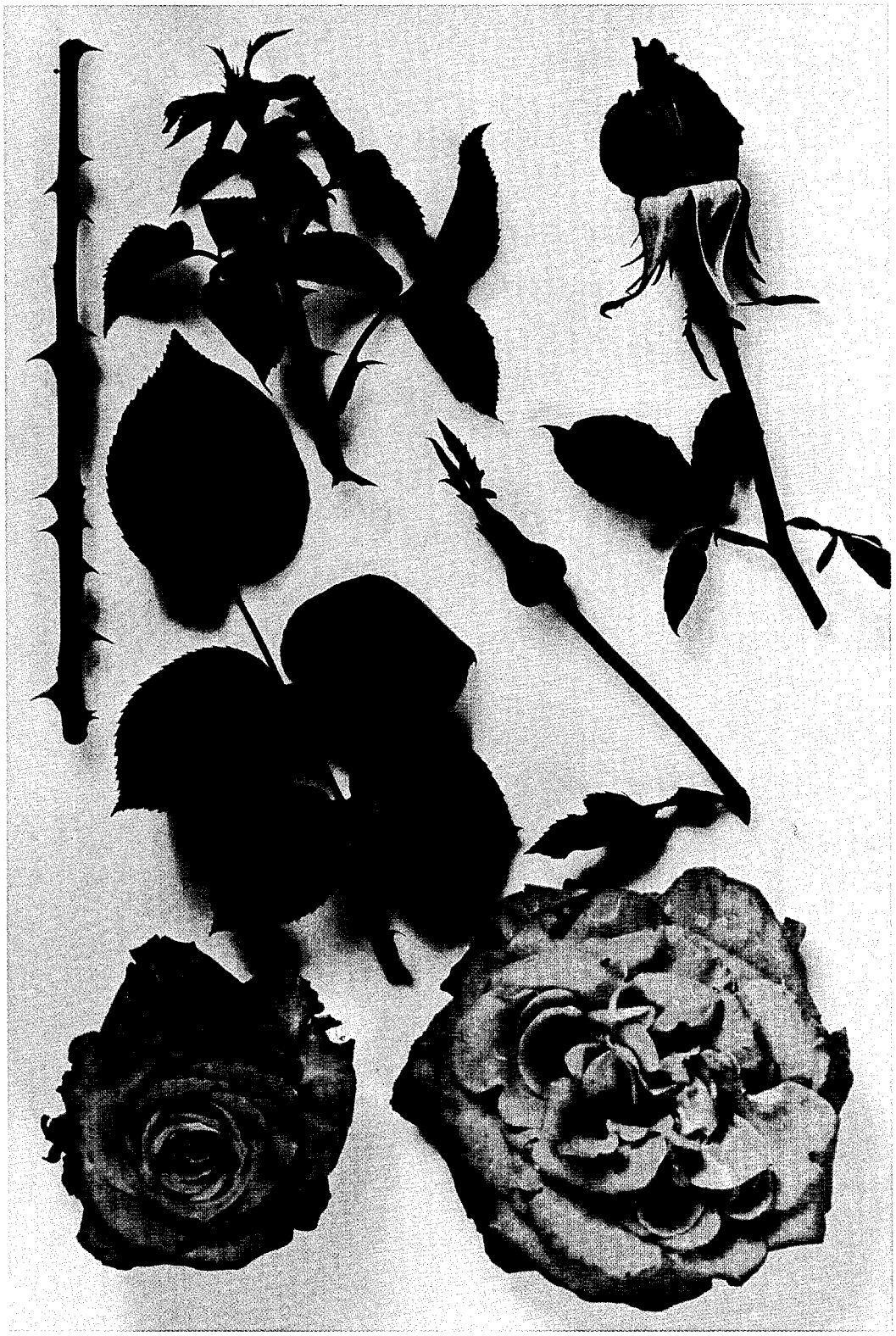

* * * * *